US011135050B2

(12) United States Patent
Kringle et al.

(10) Patent No.: US 11,135,050 B2
(45) Date of Patent: Oct. 5, 2021

(54) STENT INCLUDING ANCHORING MEMBERS

(71) Applicant: BOSTON SCIENTIFIC SCIMED, INC., Maple Grove, MN (US)

(72) Inventors: Mark Kringle, Minneapolis, MN (US); Devon N. Arnholt, Shoreview, MN (US); Mark W. Boden, Harrisville, RI (US); David Shreeve, Northborough, MA (US); Christopher Macomber, Wayzata, MN (US); Danilo B. Decio, Worcester, MA (US); Mitchell Cahan, Holden, MA (US); Pradeep P. Nazarey, Shrewsbury, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 606 days.

(21) Appl. No.: 15/723,338

(22) Filed: Oct. 3, 2017

(65) Prior Publication Data

US 2018/0092732 A1 Apr. 5, 2018

Related U.S. Application Data

(60) Provisional application No. 62/403,813, filed on Oct. 4, 2016.

(51) Int. Cl.
*A61F 2/848* (2013.01)
*A61F 2/04* (2013.01)
(Continued)

(52) U.S. Cl.
CPC .................. *A61F 2/04* (2013.01); *A61F 2/07* (2013.01); *A61F 2/848* (2013.01); *A61F 2/064* (2013.01);
(Continued)

(58) Field of Classification Search
CPC .... A61F 2/04; A61F 2/07; A61F 2/848; A61F 2002/045
See application file for complete search history.

(56) References Cited

U.S. PATENT DOCUMENTS 6,231,562 B1     5/2001  Khosravi et al.
6,352,553 B1 *   3/2002  van der Burg .......... A61F 2/844
                                                    623/1.23

(Continued)

OTHER PUBLICATIONS

Lamazza et al., "Endoscopic placement of self-expandable metallic stents for rectovaginal fistula after colorectal resection: a comparison with proximal diverting ileostomy alone," Surgical Endoscopy, 30:797-801, 2016.

(Continued)

*Primary Examiner* — Jerrah Edwards
*Assistant Examiner* — Christine L Nelson
(74) *Attorney, Agent, or Firm* — Seager, Tufte & Wickhem, LLP

(57) ABSTRACT

A method for treating an intestine with an expandable scaffolding expanded within the intestine. After placing the expandable scaffolding at a target location, such as across a fistula, the first and second end portions of the expandable scaffolding are radially expanded such that the first and second end portions contact an inner surface of the intestine on opposing sides of the fistula, anchoring the first and second end portions to the intestine. Radially expanding the first and second end portions foreshortens the medial portion along the longitudinal axis such that the first and second end portions are drawn closer together along the longitudinal axis as the medial portion foreshortens to close the fistula.

15 Claims, 9 Drawing Sheets

(51) Int. Cl.
*A61F 2/07* (2013.01)
*A61F 2/91* (2013.01)
*A61F 2/06* (2013.01)
*A61F 2/966* (2013.01)
*A61F 2/90* (2013.01)

(52) U.S. Cl.
CPC . *A61F 2/90* (2013.01); *A61F 2/91* (2013.01); *A61F 2/966* (2013.01); *A61F 2002/041* (2013.01); *A61F 2002/043* (2013.01); *A61F 2002/044* (2013.01); *A61F 2002/045* (2013.01); *A61F 2002/046* (2013.01); *A61F 2002/047* (2013.01); *A61F 2002/072* (2013.01); *A61F 2002/8486* (2013.01); *A61F 2210/0004* (2013.01); *A61F 2210/0014* (2013.01); *A61F 2210/0057* (2013.01); *A61F 2210/0076* (2013.01); *A61F 2220/0008* (2013.01); *A61F 2220/0083* (2013.01); *A61F 2250/001* (2013.01); *A61F 2250/0007* (2013.01); *A61F 2250/0039* (2013.01)

(56) References Cited

U.S. PATENT DOCUMENTS

| | | |
|---|---|---|
| 7,267,694 B2 | 9/2007 | Levine et al. |
| 7,691,153 B2 | 4/2010 | Benz et al. |
| 7,695,446 B2 | 4/2010 | Levine et al. |
| 7,914,552 B2 | 3/2011 | Shelton, IV |
| 8,002,731 B2 | 8/2011 | Weitzner et al. |
| 8,007,541 B2 | 8/2011 | Benz et al. |
| 8,048,140 B2 | 11/2011 | Purdy |
| 8,298,281 B2 | 10/2012 | Majercak et al. |
| 8,348,988 B2 | 1/2013 | Lad et al. |
| 8,500,751 B2 | 8/2013 | Rudakov et al. |
| 8,715,334 B2 | 5/2014 | Clerc et al. |
| 8,801,647 B2 | 8/2014 | Melanson et al. |
| 8,876,883 B2 | 11/2014 | Rust |
| 8,915,941 B2 | 12/2014 | Obermiller et al. |
| 9,277,921 B2 | 3/2016 | Laufer |
| 9,339,272 B2 | 5/2016 | Khosrovaninejad |
| 2005/0255230 A1 | 11/2005 | Clerc et al. |
| 2006/0253190 A1 | 11/2006 | Kuo |
| 2007/0179590 A1 | 8/2007 | Lu et al. |
| 2008/0021544 A1 | 1/2008 | Majercak et al. |
| 2009/0187240 A1 | 7/2009 | Clerc et al. |
| 2009/0204064 A1 | 8/2009 | Farin et al. |
| 2009/0270977 A1 | 10/2009 | Surber et al. |
| 2010/0082056 A1 | 4/2010 | Mavani et al. |
| 2011/0087146 A1* | 4/2011 | Ryan .................. A61F 2/04 604/8 |
| 2011/0307070 A1 | 12/2011 | Clerc et al. |
| 2012/0130470 A1 | 5/2012 | Agnew et al. |
| 2012/0283811 A1 | 11/2012 | Neilan |
| 2012/0296257 A1 | 11/2012 | Van Dam et al. |
| 2012/0310363 A1 | 12/2012 | Gill et al. |
| 2013/0172983 A1 | 7/2013 | Clerc et al. |
| 2014/0222039 A1 | 8/2014 | Khosrovaninejad |
| 2014/0236186 A1 | 8/2014 | Smith et al. |
| 2014/0243950 A1 | 8/2014 | Weiner |
| 2014/0277442 A1 | 9/2014 | Seddon et al. |
| 2014/0343683 A1 | 11/2014 | Jeon et al. |
| 2016/0338864 A1* | 11/2016 | Vad .................. A61F 2/966 |
| 2017/0290653 A1* | 10/2017 | Folan .................. A61F 2/90 |

OTHER PUBLICATIONS

Branche, et al., "Extractible self-expandable metal stent in the treatment of Crohn's disease anastomotic strictures," Endoscopy, 44: E325-E326, 2012.

Ahluwalia et al., "Human small intestinal contractions and aboral traction forces during fasting and after feeding," Gut, 35: 625-630, 1994.

Gayer et al., "The effects of mechanical forces on intestinal physiology and pathology," Cell Signal, 21(8): 1237-1244, Aug. 2009.

Tsereteli et al., "Placement of a covered polyester stent prevents complications from a colorectal anastomotic leak and supports healing: Randomized controlled trial in a large animal model," Surgery 144(5): 786-792, Nov. 2008.

Laulicht et al., "Understanding gastric forces calculated from high-resolution pill tracking," PNAS, 107(18): 8201-8206, May 4, 2010.

Karstensen et al., "Successful endoscopic treatment of a 12-cm small-bowel Crohn stricture with a custom-made biodegradable stent," Endoscopy, 46: E227-E228, 2014.

Ho et al., "Techniques for colorectal anastomosis," World Journal of Gastroenterology, 16(13): 1610-1621, Apr. 7, 2010.

Ehrlein et al., "Gastrointestinal motility," Humanbiology [online]. Retrieved from the internet: http://humanbiology.wzw.tum.de/motvid01/tutorial.pdf., Dec. 12, 2017.

* cited by examiner

STENT INCLUDING ANCHORING MEMBERS

CROSS-REFERENCE TO RELATED APPLICATIONS

This application claims priority under 35 U.S.C. § 119 to U.S. Provisional Application Ser. No. 62/403,813, filed Oct. 4, 2016, the entirety of which is incorporated herein by reference.

TECHNICAL FIELD

The present disclosure pertains to medical devices, and methods for manufacturing medical devices. More particularly, the present disclosure pertains to an expandable scaffold including anchoring members and methods for manufacturing and using such devices.

BACKGROUND

A fistula is an abnormal opening between two organs in the body. In some instances, a fistula opening may permit bodily fluid to flow between the two organs. For example, a gastrointestinal fistula is an abnormal opening in the intestinal wall. The opening in the intestinal wall may allow gastric fluid to leak from the intestine into the abdominal cavity. Further, the leakage may allow other organs to come in contact with the gastric fluid, potentially causing the surrounding tissue and organs to become infected. Therefore, it may be desirable to design medical devices which cover fistula openings, thereby preventing intestinal fluid leakage to surrounding tissue and organs.

BRIEF SUMMARY

This disclosure provides design, material, manufacturing method, and use alternatives for medical devices. An example method for treating an intestine includes advancing an expandable scaffold to a target site within the intestine, the expandable scaffold including a first end portion, a second end portion and a medial portion extending along a longitudinal axis of the scaffold. The medial portion is positioned between the first portion and the second portion. The expandable scaffold is configured to shift from a contracted state to an expanded state. The method further includes radially expanding the first and second end portions from the contracted state to the expanded state such that the first and second end portions contact an inner surface of the intestine in the expanded state, anchoring the first and second end portions to the intestine with one or more anchoring members to prevent the first and second end portions from shifting along the inner surface of the intestine, wherein radially expanding the first and second end portions foreshortens the medial portion along the longitudinal axis such that the first and second end portions are drawn closer together along the longitudinal axis as the medial portion foreshortens.

Alternatively or additionally to any of the embodiments above, the medial portion is spaced away from the inner surface of the intestine when in the expanded state.

Alternatively or additionally to any of the embodiments above, the scaffold is configured to provide a pathway for food to travel therethrough.

Alternatively or additionally to any of the embodiments above, the medial portion includes a retaining member, the retaining member configured to prevent the medial portion from foreshortening before the first and second end portions have at least partially shifted to the expanded state.

Alternatively or additionally to any of the embodiments above, the retaining member substantially surrounds the medial portion such that the medial portion is prevented from foreshortening before the first and second end portions have at least partially shifted to the expanded state.

Alternatively or additionally to any of the embodiments above, the retaining member includes a filament, the filament including a first end, and wherein the filament is configured to release the medial portion as the first end is retracted.

Alternatively or additionally to any of the embodiments above, the medial portion is maintained in the contracted state until after the first and second end portions are fully expanded.

Alternatively or additionally to any of the embodiments above, the filament is retracted after the first and second end portions are at least partially deployed.

Another example method for treating an intestine includes advancing an expandable scaffold to a target site within the intestine. The expandable scaffold includes a first end portion, a second end portion and a medial portion extending along a longitudinal axis of the scaffold. The medial portion is positioned between the first end portion and the second end portion. The expandable scaffold is configured to shift from a contracted state to an expanded state. The expandable scaffold also includes a retaining member releasably attached to the medial portion. The method includes radially expanding the first and second end portions from the contracted state to the expanded state such that the first and second end portions contact the inner surface of the intestine in the expanded state. The method also includes anchoring the first and second end portions to the intestine with one or more anchoring members to prevent the first and second end portions from shifting along the inner surface of the intestine.

Alternatively or additionally to any of the embodiments above, the retaining member is released to allow the medial portion to expand, wherein releasing the retaining member foreshortens the medial member along the longitudinal axis to draw the first and second end portions closer together in the expanded state.

Alternatively or additionally to any of the embodiments above, the medial portion is spaced away from the inner surface of the body lumen in the expanded state.

Alternatively or additionally to any of the embodiments above, the retaining member substantially surrounds the medial portion such that the medial portion is prevented from foreshortening before the first and second end portions have at least partially shifted to the expanded state.

Alternatively or additionally to any of the embodiments above, the retaining member includes a filament, the filament including a first end, and wherein the filament is configured to release the medial portion to allow radial expansion as the first end is retracted.

Alternatively or additionally to any of the embodiments above, the medial portion is maintained in a contracted state until after the first and second end portions are fully expanded.

Alternatively or additionally to any of the embodiments above, the filament is retracted after the first and second end portions are at least partially deployed.

An example medical device for treating an intestine includes an expandable scaffold including a first end portion, a second end portion and a medial portion extending along a longitudinal axis of the scaffold. The medial portion is positioned between the first end portion and the second end portion. The expandable scaffold is configured to shift from a contracted state to an expanded state. Each of the first and second end portions include one or more anchoring members configured to anchor the first and second end portions to an inner surface of the intestine to prevent the first and second end portions from shifting along an inner surface of the intestine when the first and second end portions are positioned adjacent the inner surface of the intestine in the expanded state. The medial portion is configured to foreshorten along the longitudinal axis when shifting from the contracted state to the expanded state such that the first and second end portions are drawn closer together along the longitudinal axis as the medial portion shortens.

Alternatively or additionally to any of the embodiments above, the medial portion is configured to be spaced away from the inner surface of the intestine when the first and second end portions are expanded.

Alternatively or additionally to any of the embodiments above, the device includes a retaining member configured to retain the medial portion in a contracted state while the first and second end portions expand to the expanded state.

Alternatively or additionally to any of the embodiments above, releasing the retaining member foreshortens the medial member along the longitudinal axis to draw the first and second end portions closer together in the expanded state.

Alternatively or additionally to any of the embodiments above, the retaining member includes a filament that substantially surrounds the medial portion such that the medial portion is prevented from foreshortening before the first and second end portions have at least partially shifted to the expanded state.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
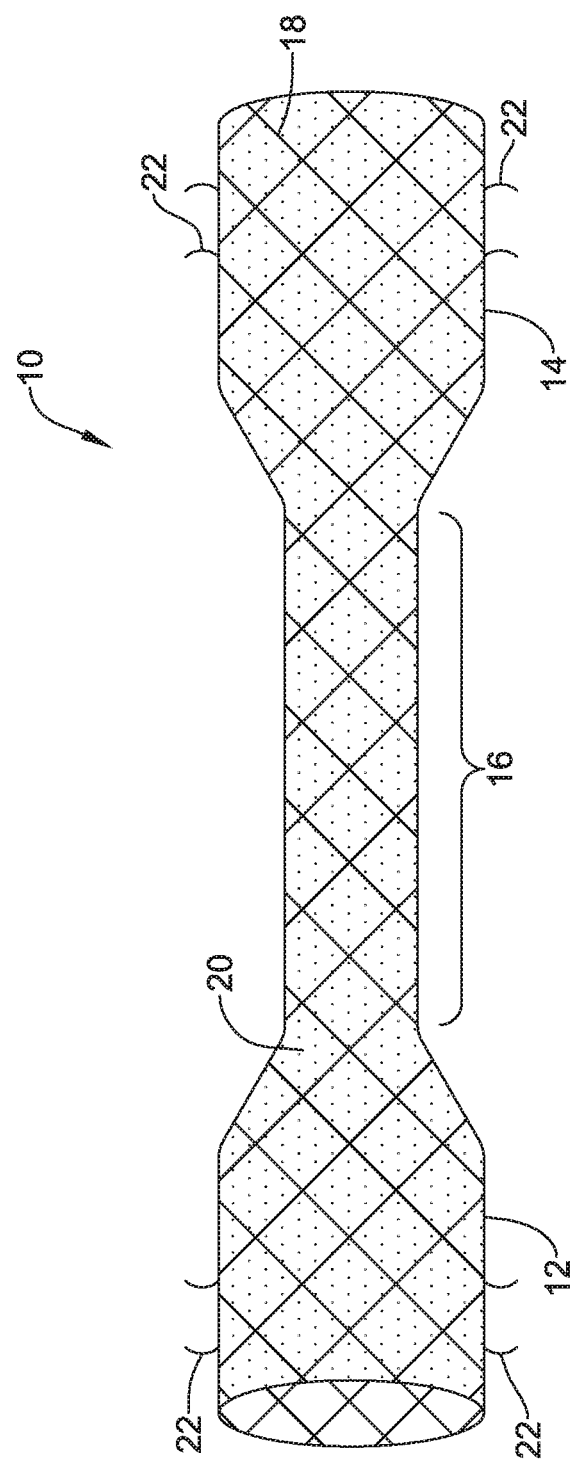
FIG. 1 illustrates an example stent including anchoring members.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As discussed above, a fistula is an abnormal opening between two organs in the body. In some instances, a fistula opening may permit bodily fluid to flow between the two organs. For example, a gastrointestinal fistula is an abnormal opening in the intestinal wall. The opening in the intestinal wall may allow gastric fluid to leak from the intestine into the abdominal cavity. Further, the leakage may allow other organs to come in contact with the gastric fluid, potentially causing the surrounding tissue and organs to become infected. Therefore, it may be desirable to design medical devices which cover fistula openings, thereby preventing intestinal fluid leakage to surrounding tissue and organs.

In some instances, a fistula or other opening in a body lumen may not be able to completely heal if digested material (e.g., digested food, liquids, etc.) continually passes through (e.g., leaks through) the fistula as it travels through the body lumen of the gastrointestinal tract (e.g., the intestine). In order for the body to naturally heal a fistula site, the fistula site needs to be kept clean, which reduces tissue inflammation around the fistula site.

In some instances, a medical device may be designed to help cover and/or close a fistula or other opening. For example, examples disclosed herein may include a tubular member having a covering and/or one or more anchoring members designed to prevent the tubular member from shifting with respect to the opening. The medical device may further cover the fistula, thereby preventing fluid from leaking therethrough. Therefore, some examples disclosed herein span and cover the fistula in order to provide a conduit (e.g., a bypass) for food or other digested material to pass through the body lumen without disturbing the tissue surrounding and/or adjacent to the fistula. For example, examples disclosed herein may include a stent, such as a self-expanding stent, including a covering and one or more anchoring members positioned on an outer surface thereof. The anchoring members may allow the stent to draw the ends of the fistula together, thereby permitting self-healing of the opening. Additionally, the stent covering permits food and other digested materials to pass therethrough without directly contacting the fistula or adjacent tissue.

FIG. 1 illustrates an example implantable medical device 10. Implantable medical device 10 may be configured to be positioned in a body lumen for a variety of medical applications. For example, implantable medical device 10 may be used to treat a fistula or other opening in a body lumen. For example, medical device 10 may be used to span and cover a fistula located in an intestine and provide a pathway for food or other digested materials to pass therethrough without directly contacting the fistula or adjacent tissue. Additionally, it is contemplated that the examples described herein may be utilized in other regions of the gastrointestinal tract, as well as in the vascular, urinary, biliary, tracheobronchial, esophageal, or renal tracts, for example. In some instances, implantable medical device 10 may be an expandable scaffold such as a stent (e.g., an intestinal stent, a vascular stent, tracheal stent, bronchial stent, esophageal stent, etc.). However, although illustrated as a stent, implantable medical device 10 may be any of a number of devices that may be introduced endoscopically, subcutaneously, percutaneously or surgically to be positioned within an organ, tissue, or lumen, such as an intestine, colon, urethra, esophagus, trachea, bronchus, bile duct, blood vessel, or the like.

Implantable medical device 10 may have a first end portion 12 extending to a first end of the implantable medical device 10 and a second end portion 14 extending to a second end of the implantable medical device 10 opposite the first end. First end portion 12 and second end portion 14 may be attached together via a medial portion 16 along the length of the implantable medical device 10 to form an expandable tubular framework with open ends and defining a lumen extending therein. In other words, medial portion 16 may be positioned between first end portion 12 and second end portion 14. First end portion 12 and/or second end portion 14 may include a flared end portion, if desired. For example, first end portion 12 and/or second end portion 14 may have an outer diameter that is greater than the outer diameter of the medial portion 16. Additionally, first end portion 12, second end portion 14 and medial portion 16 may extend along a central longitudinal axis of medical device 10.

A plurality of strut members 18 may be arranged in a variety of different designs and/or geometric patterns to form stent 10. Numerous designs, patterns and/or configurations for the stent cell openings, strut thicknesses, strut designs, stent cell shapes are contemplated and may be utilized with embodiments disclosed herein. Further, self-expanding stent examples disclosed herein may include stents having one or more strut members 18 combined to form a rigid and/or semi-rigid stent structure. For example, strut members 18 may be wires or filaments braided, intertwined, interwoven, weaved, knitted, crocheted or the like to form the stent structure. The strut members (e.g., wires or filaments) 18 of medical device 10 may be configured to self-expand to an expanded diameter when unconstrained. Alternatively, strut members 18 may be formed from a monolithic structure (e.g., a cylindrical tubular member), such as a single, cylindrical tubular laser-cut Nitinol tubular member, in which the remaining portions of the tubular member form the strut members 18. The monolithic structure of stent 10 may be configured to self-expand to an expanded diameter when unconstrained.

Stent 10 in at least some examples disclosed herein may be constructed from a variety of materials. For example, stent 10 may be constructed from a metal (e.g., Nitinol). In other instances, stent 10 may be constructed from a polymeric material (e.g., PET). In yet other instances, stent 10 may be constructed from a combination of metallic and polymeric materials. Additionally, stent 10 may include a bioabsorbable and/or biodegradable material.

In some instances, example stent 10 may include one or more layers (e.g., covering, coating, etc.) 20 of material positioned on and/or adjacent to the outer and/or inner surface of stent 10 (depicted by the dotted pattern in FIG. 1). In some instances, covering 20 may be an elastomeric or non-elastomeric material. Covering 20 may be formed from a suitable material. For example, the layer or covering 20 may be a polymeric material, such as silicone, polytetrafluoroethylene, polyurethane, or the like, or other materials including those disclosed herein. In some examples, covering 20 may be bioabsorbable and/or biodegradable. In other examples, covering 20 may be biostable. Coupling covering 20 to strut members 18 may include thermal bonding, molding, spray coating, dip coating, extruding, adhering, or the like.

In some instances, covering 20 may be disposed along an outer or inner surface of strut members 18. In other instances, covering 20 may be disposed along both an inner and an outer surface of stent strut members 18. In some of these and in other instances, covering 20 may encapsulate strut members 18 or otherwise have strut members 18 embedded (e.g. partially or fully embedded) therein. Further, the covering 20 may span the spaces (e.g., openings, cells, interstices) between struts or filaments 18 of stent 10, thus providing a fully covered stent.

Additionally, covering 20 may cover the entire surface area of stent 10 (e.g., the covering 20 may span all of struts or filaments 18). However, it is also contemplated that covering 20 may cover only a portion of stent 10. For example, it is contemplated that covering 20 may only cover medial portion 16 (or, alternatively, only cover a portion of medial portion 16.) Further, covering 20 (or a portion thereof) may extend around the entire circumference of stent 10. Additionally, covering 20 may only extend partially around the circumference of stent 10. For example, covering 20 may extend along only one side of stent 10 or cover only a select portion of stent 10 (e.g., covering 20 may only cover the location of particular fistula or opening in a body lumen).

In other examples disclosed herein, stent delivery system may 10 may include a flexible polymeric sheath which has no underlying stent support. For example, stent 10 may include a sheath or film (e.g., cylindrical foam) that may be expanded similar to how stent 10 may be expanded.

The covering 20 disclosed herein may be configured such that digested material (e.g., digested food, liquids, etc.) cannot pass from an inner surface of the covering 20 to the outer surface of the covering 20. In other words, when positioned on the outer and/or inner surface of stent 10, the covering may permit food to pass through the inner lumen of stent 10 without leaking from the inner surface to the outer surface of the covering 20. Thus, covering 20 may extend fully circumferentially around stent 10 at least along the medial portion 16 of stent 10, and may, in some instances, extend from one end of stent 10 to the opposite end of stent 10 and cover the first and second end portions 12, 14.

Stent 10 may be designed to include one or more anchoring members 22. The one or more anchoring members 22 may be positioned on and extend radially outward away from the outer surface of stent 10 and be configured to contact an inner surface of the body lumen (e.g., intestine). For example, in at least some examples disclosed herein, anchoring members 22 may include a projection extending radially outward away from the outer surface of stent member 10 to engage and/or penetrate into the wall of the body lumen, (e.g., intestine). In some examples, anchoring members 22 may include a barb, hook, point, spike, spur, rib, circumferential rim, prong, etc. However, in other examples, the anchoring members 22 may include a bump or similar protuberance extending radially outward away from the outer surface of stent 10. For example, anchoring members 22 may be defined as a collection of projections and/or raised features that collectively define a surface texture (e.g., a knurled pattern or similar texture). In other instances, anchoring members 22 may include adhesive, sutures or clips configured to engage the wall of the body lumen. In yet other instances, anchoring members 22 may include a combination of a suture, clip, barb, hook, point, spike, spur, rib, circumferential rim, prong, bump, protuberance, adhesive, etc. and other surface textures. Other anchoring configurations and/or methods designed to increase friction between stent 10 and the inner surface of a body lumen in order to limit or prevent distal movement of stent 10 are contemplated.

It can be appreciated that the anchoring members 22 described above may be configured to prevent stent 10 from shifting longitudinally or migrating relative to an inner surface of a body lumen when stent 10 is positioned adjacent a target site (e.g., when placed adjacent a fistula in the intestine). In some instances, anchoring members 22 that include a suture, clip, barb, hook, point, spike, spur, rib, circumferential rim, prong, bump, protuberance, etc. may be configured to project into and/or through the wall of a body lumen, thereby affixing the anchoring member 22 into the tissue of the body lumen (e.g., intestine) and preventing stent 10 from longitudinally shifting or migrating with respect to the body lumen. However, in other instances the anchoring members 22 that include a surface texture and/or adhesive may be configured to remain on the inner surface of the body lumen, thereby not extending into the wall of a body lumen. Anchoring members 22 including a surface texture and/or adhesive may create friction and/or adhesion with the tissue of the body lumen (e.g., the inner surface of the intestine), which may prevent stent 10 from longitudinally shifting or migrating with respect to the body lumen.

Anchoring members 22 may be designed to resist forces that may be imparted to stent 10 via peristalsis in the intestine. For example, anchoring members 22 may need to overcome sheer stresses placed on the stent 10. The anchoring members 22 may need to be able to overcome a range of shear stress. For example, the shear stress imparted to a stent positioned in a body lumen (e.g., intestine) varies widely between individuals. Factors such as the exact placement of the device within a particular body lumen and the type of vessel being treated may influence the shear stress placed upon the stent. It is contemplated that the examples disclosed herein are designed to overcome a wide range of shear stress in order to prevent stent migration at any given target site.

Figure 2:
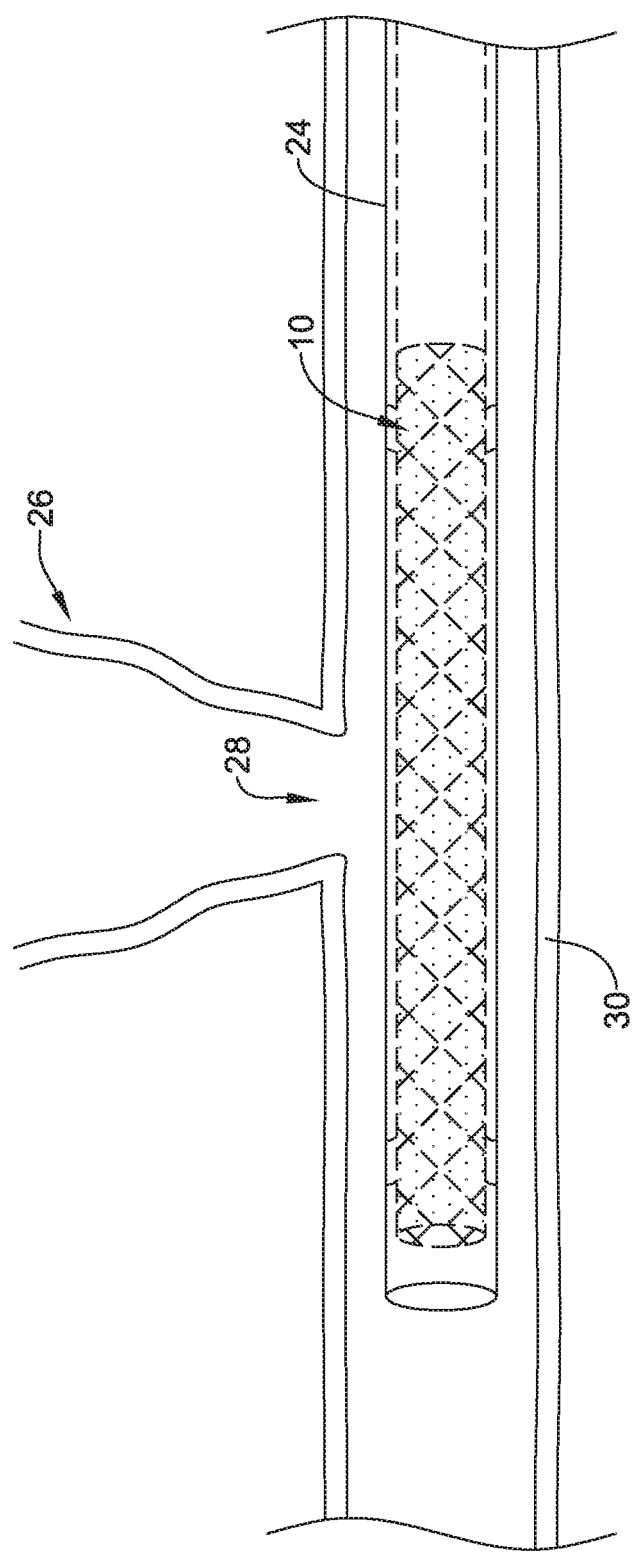
FIG. 2 illustrates an example stent positioned adjacent a fistula.

FIG. 2 shows stent 10 positioned within an example stent delivery sheath 24 adjacent a fistula 26 (located in an intestinal wall 30). Fistula 26 may include an opening 28 which extends through the intestinal wall 30. It can be appreciated, therefore, that, absent a covering spanning across opening 28, digested material (e.g., food, liquid) may pass from the intestine, through opening 28 of the fistula 26 and into the abdominal cavity. This continuous flow of material through the fistula opening 28 may result in the inability of the fistula 26 to heal itself, as material passing through opening 28 prevents the edges of the opening 28 from being drawn together and eventually closing.

FIGS. 2-5 illustrate example stent 10 and a sequence of steps showing the deployment of stent 10 from stent delivery sheath 24. In at least some examples, it can be appreciated that stent delivery sheath 24 is configured to shift between a first position, for example as shown in FIG. 2, where sheath 24 overlies or surrounds stent 10 and a second position where stent 10 is uncovered or retracted from sheath 24, such as when sheath 24 is proximally retracted to a position substantially proximal of stent 10. In general, the first position may be utilized during navigation and delivery of stent 10 to the appropriate location within a body lumen (e.g., fistula 26 within intestine 30) and the second position may be used to deploy stent 10.

Figure 3:
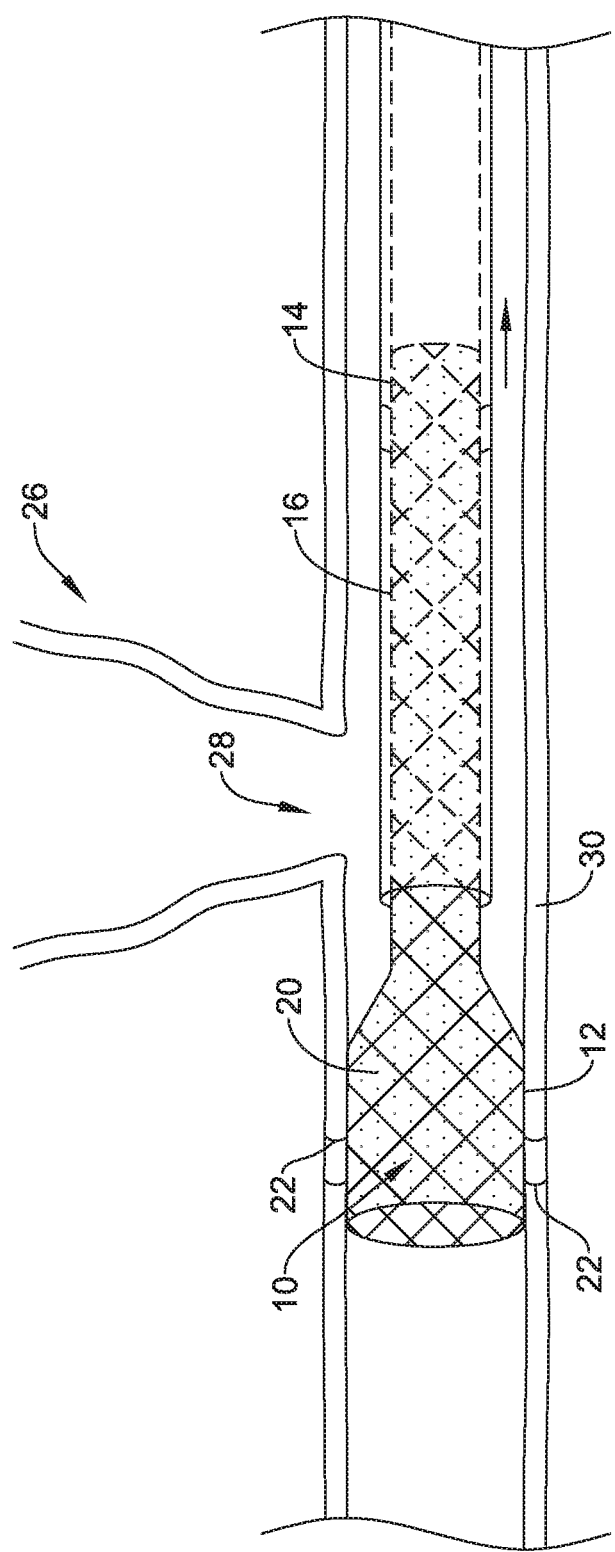
FIG. 3 illustrates the example stent of FIG. 2 being deployed adjacent the fistula.

FIG. 3 further illustrates an example step in the deployment of stent 10 within example body lumen 30. It can be appreciated that prior to the deployment step illustrated in FIG. 3, stent 10 may have been navigated to a position adjacent a target site (e.g., fistula 26) in body lumen 30. Once navigated to a desired location, a clinician or other operator may retract sheath 24 relative to stent 10. As stated above, stent 10 may be a self-expanding stent biased to expand radially outward when unconstrained, while in other embodiments stent 10 may be balloon expandable or otherwise radially expandable. FIG. 3 further illustrates that as sheath 24 is retracted in a proximal direction (thereby exposing first end portion 12), the exposed portion of stent 10 may automatically radially expand outward toward the inner surface of body lumen 30. FIG. 3 illustrates the first end portion 12 expanding radially outward as retraction sheath 24 is translated in a proximal direction (as depicted by the proximal pointing arrow in FIG. 3).

FIG. 3 further illustrates that first end portion 12 may radially expand to a position in which the outer surface of first end portion 12 contacts the inner wall of body lumen 30. Additionally, as described above, FIG. 3 illustrates that one or more anchoring members 22 may engage (e.g., anchors 22 which penetrate the tissue surface) and/or interface or engage with the wall (e.g., anchors 22 which create a frictional interface and/or adhere to the wall) with the inner surface and/or wall of body lumen 30. It can be appreciated that any of the mechanisms described herein to prevent shifting of stent 10 relative to body lumen 30 may also assist in creating a tight seal of the outer surface of the first and second end portions 12/14 with the inner surface of the intestine 30. This seal prevents digested material from leaking around stent 10 (i.e., passing along the exterior of stent 10 between the outer surface of stent 10 and the wall of body lumen 30, and contacting fistula 26 and/or passing through the opening 28 of fistula 26.

Figure 4:
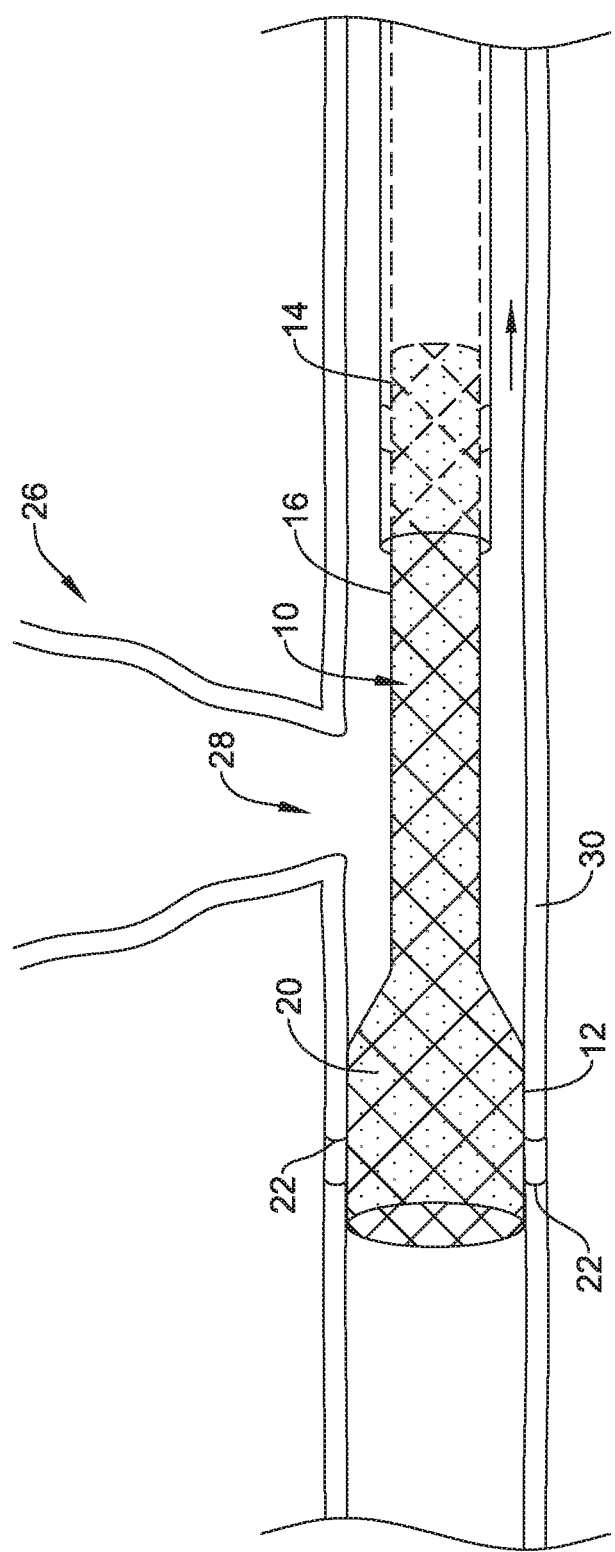
FIG. 4 illustrates the example stent of FIG. 2 being deployed adjacent the fistula.

FIG. 4 illustrates an example second step in the deployment of example stent 10. As shown in FIG. 4, retraction sheath 24 may be retracted in a proximal direction such that the medial portion 16 of stent 10 is uncovered. As described above, the outer diameter of the medial portion 16 of stent 10 may be smaller than the diameter of the first and second end portions 12/14 of stent 10 when radially expanded. Therefore, as illustrated in FIG. 4, the medial portion 16 of stent 10 may be spaced away from the inner surface of body lumen 30 when deployed from delivery sheath 24. This spacing may be desirable as it allows the opening 28 of fistula 26 to remain spaced away from and thus remain free of stent 10 rubbing against it and/or any digested material from passing through the opening 28.

Figure 5:
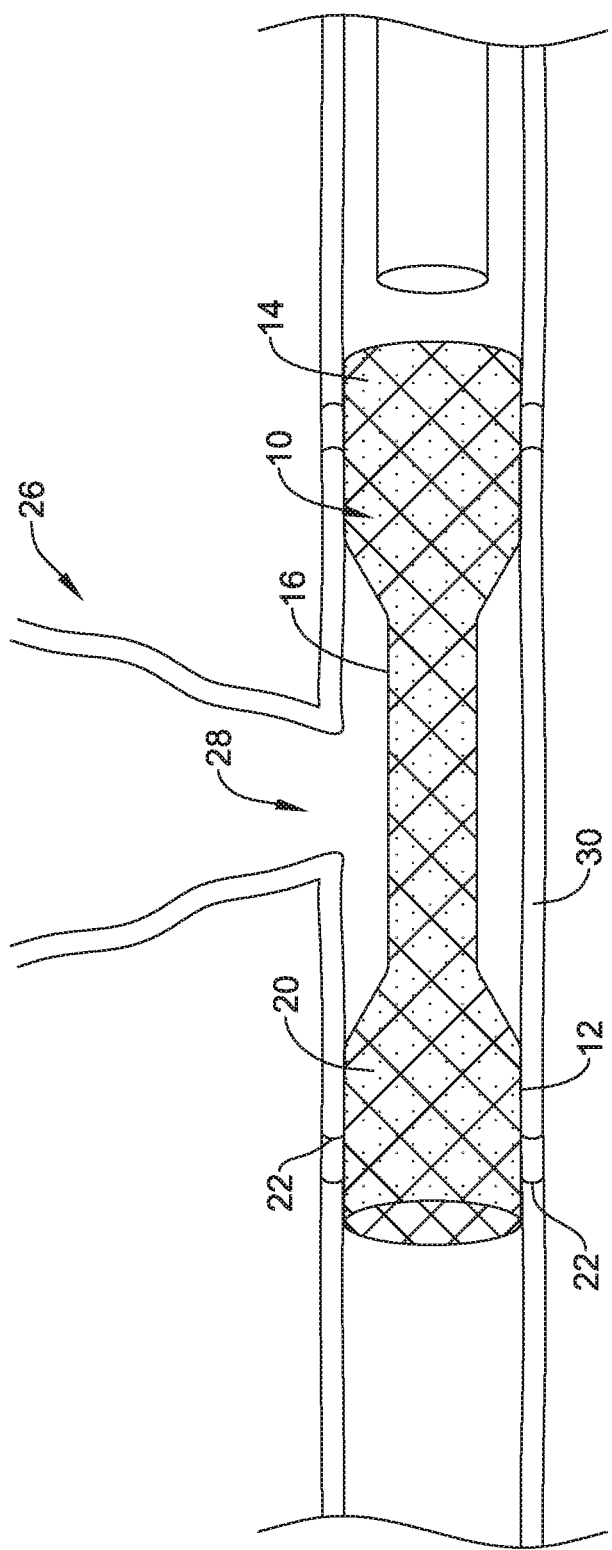
FIG. 5 illustrates the another example stent being deployed adjacent a fistula.

FIG. 5 illustrates an example third step in the deployment of example stent 10. As shown in FIG. 5, retraction sheath 24 may be completely retracted in a proximal direction such that the second end portion 14 of stent 10 is uncovered. Similar to the description above with respect to the deployment of the first end portion 12, second end portion 14 may radially expand to a position in which the outer surface of second end portion 14 contacts the inner wall of body lumen 30. Additionally, as described above, FIG. 5 illustrates that one or more anchoring members 22 may engage (e.g., anchors 22 which penetrate the tissue surface) and/or interface or engage with the wall (e.g., anchors 22 which create a frictional interface and/or adhere to the wall) with the inner surface and/or wall of body lumen 30. As stated above, it can be appreciated that the attachment mechanisms described herein to prevent shifting of second end portion 14 relative to body lumen 30 may also assist in creating a tight seal of the outer surface of second end portion 14 with the inner surface of the intestine 30, preventing digested material from leaking around stent 10.

It can be appreciated from FIG. 5 that when stent 10 is fully deployed within body lumen 30, and both the first end portion 12 and second end portion 14 are radially expanded and sealed to the lumen wall, stent 10 may create a passageway therethrough in which digested material may pass without disturbing opening 28 of the fistula 26.

While the above discussion describes the anchoring members as being able to penetrate the body lumen wall and/or create friction with the body lumen wall, other mechanisms are contemplated to secure the first and second end portions 12/14 to the body lumen. For example, stent 10 may include sutures and/or stitches which secure the first and second portions 12/14 to body lumen 30. Further, stent 10 may include a tacky material, membrane or film which adheres to the inner surface of body lumen 30. Additionally, stent 10 may include drawstrings which secure the first and second portions 12/14 to body lumen 30. Combinations of any of the securement methods described herein are also contemplated.

FIGS. 6-9 illustrate another example stent delivery system 110 and a sequence of steps showing the deployment of stent 110 from example stent delivery sheath 124. It is noted that the stent 110 illustrated in FIGS. 6-9 may be substantially similar in form and its method of functionality to the stent 10 and delivery sheath 24 described above with respect to FIGS. 2-5. However, in some instances it may be desirable to further configure stent 110 with the ability to foreshorten (i.e., retract in longitudinal length) during deployment. Additionally, it may be desirable to design stent 110 such that a clinician may control when stent 110 foreshortens. To that end, FIGS. 6-9 illustrate an example stent 110 which may be deployed in two stages: the first stage in which the first and second end regions 12/14 radially expand to contact the inner surface of lumen 30 (as described above with respect to FIGS. 2-5), and a second stage in which the medial portion 16 is expanded (e.g., released) and foreshortened.

Figure 6:
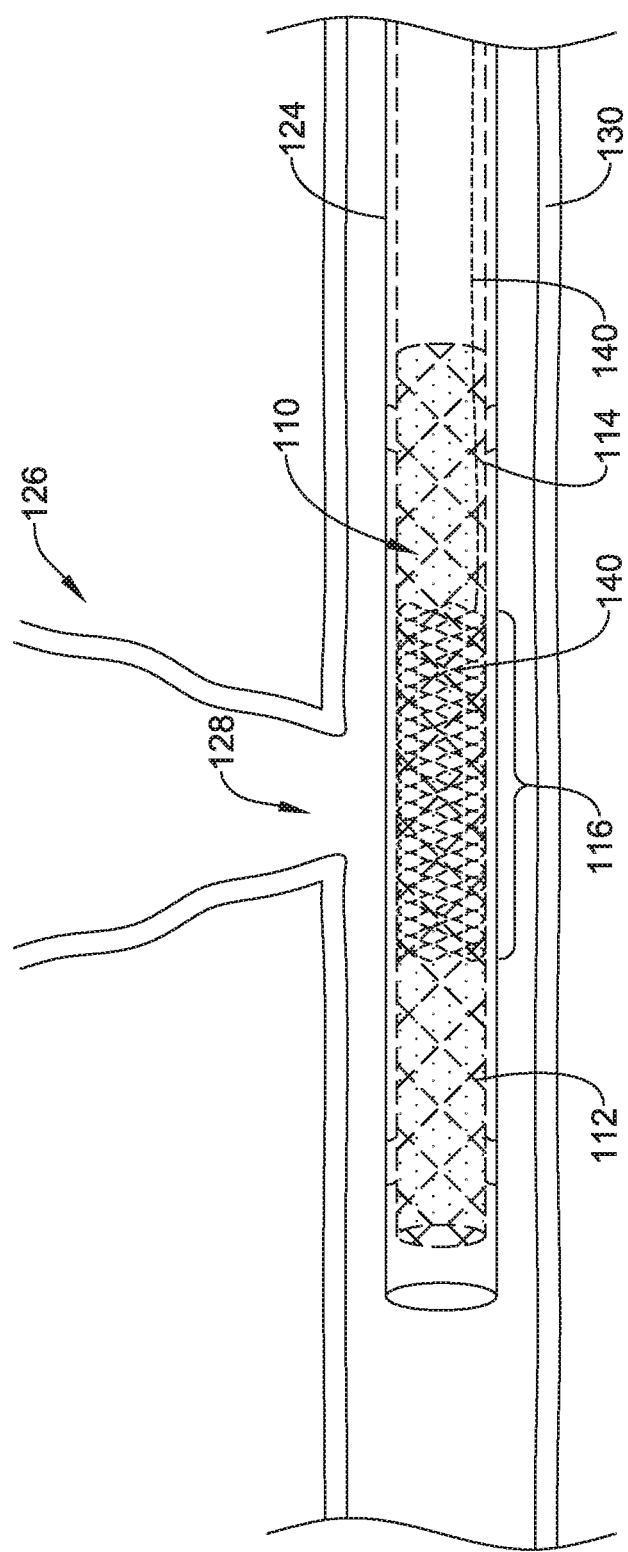
FIG. 6 illustrates the example stent of FIG. 5 being deployed adjacent the fistula.

FIG. 6 illustrates stent 110 which is substantially similar to stent 10 described above. However, FIG. 6 further illustrates stent 110 includes a retaining member 140 associated with and/or disposed along the medial portion 116 of stent member 110. The retaining member 140 illustrated in FIG. 6 may include any structure that can maintain medial portion 116 in a contracted (e.g., constrained) state until the retaining member is actuated, removed, or otherwise manipulated thereby permitting medial portion 116 to radially expand. As stated above, in at least some of the examples described herein, radial expansion of the medial portion 116 may cause the medial portion 116 to correspondingly foreshorten. In other words, radial expansion of the medial portion 116 may cause the longitudinal length of medial portion 116 measured along the central longitudinal axis of stent 110 to decrease, drawing the first and second end portions 112/114 closer together.

In some examples, such as that illustrated in FIG. 6, retaining member 140 may include a filament which has been woven, braided, wrapped, etc. such that it maintains medial portion 116 in a constrained state until a clinician decides to remove the retaining member 140. For example, in some instances the filament may be wrapped (e.g., helically wrapped) around the circumference of medial portion 116 and/or woven or braided into the medial portion 116 and/or a sleeve wrapped around the circumference of medial portion 116.

As shown in FIG. 6 and described above, retaining member 140 may be defined by a single filament. Further, retaining member 140 may be knitted in a manner which permits it to release and/or unravel into a single, continuous filament. For example, a filament defining retaining member 140 may be configured as a knitted, generally cylindrical matrix that, upon the appropriate actuation, can be released from a first configuration (e.g., constrained) to a second configuration (e.g., into an expanded configuration). While FIG. 6 may depict retaining member 140 to be configured in a particular pattern, it can be appreciated that a variety of patterns, loops, designs, weaves, etc. may be utilized to construct retaining member 140 having the properties (e.g., ability to unravel) as described herein.

Additionally, while the above discussion describes retaining member 140 as including a woven/braided/knitted filament, it is contemplated that retaining member 140 may include other configurations which do not include filaments. For example, retaining member 140 may include a solid sheet-like structure which surrounds medial portion 116, the solid sheet-like structure configured to tear-away, bio-absolve, bio-erode, or otherwise release medial portion 116. Further, while retaining member 140 may include a filament, the filament may not be woven/braided. The filament may be positioned to around medial portion 116 such that it maintains medial portion 116 in a contracted configuration without employing a weave, knit and/or braid.

Further, other configurations and/or methods of retaining and releasing medial portion 116 are contemplated. For example, retaining member 140 may include a solid or flexible tube mounted on the inner surface of stent member 110. For example, the retaining member may include one or more hooks engage the filaments of stent 110. The hooks may face a given circumferential direction when engaged with stent 110. The retaining member 140 may be disengaged from stent 110 in a variety of manners. For example, upon rotating the retaining member 140 in a direction opposite to the circumferential direction of the hooks, the hooks may disengage from the filaments of stent 110, thereby allowing stent 110 to expand. Other methods are envisioned to constrain stent 110 using a retaining member 140 on or partially on the interior of stent 110.

As discussed above, it may be desirable to deploy stent member 110 in two stages. FIG. 6 shows stent member 110 positioned within a stent delivery sheath 124 adjacent a fistula 126 (located in an intestinal wall 130). Fistula 126 may include an opening 128 which extends through the intestinal wall 130.

Figure 7:
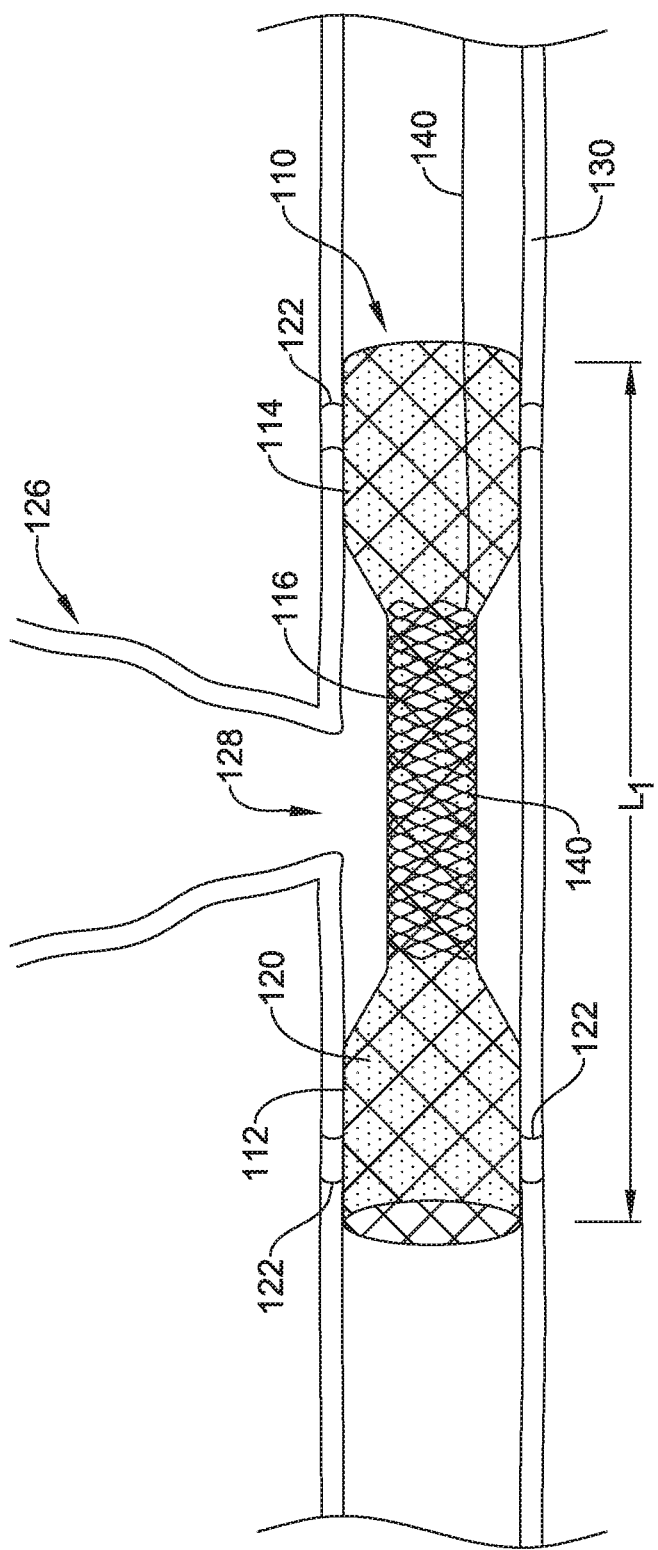
FIG. 7 illustrates the example stent of FIG. 5 being deployed adjacent the fistula.

FIG. 7 illustrates an example second step in the deployment of example stent 110. As shown in FIG. 7, after retraction sheath 124 is fully retracted in a proximal direction, first end portion 112, medial portion 116 and second end portion 114 of stent 110 may be uncovered. Further, as described above, the medial portion 116 of stent 110 may be maintained in a constrained state by retaining member 140 which has not yet been removed from medial portion 116 while first and second end portions 112/114 are radially expanded against the wall of body lumen 130. Further, FIG. 7 shows that the first and second end portions 112/114 of stent 110 have been fully deployed and are anchored and sealed against the inner surface of lumen 130 via anchoring members 122 (as described above with respect to FIGS. 1-5). Further, as illustrated in FIG. 7, the medial portion 116 of stent 110 may be spaced away from the inner surface of body lumen 130, and thus have a smaller outer diameter than first and second end portions 112/114. Additionally, after deployment and anchoring of first end portion 112 and second end portion 114, FIG. 7 illustrates that stent member 110 has a deployed length of "$L_1$."

Figure 8:
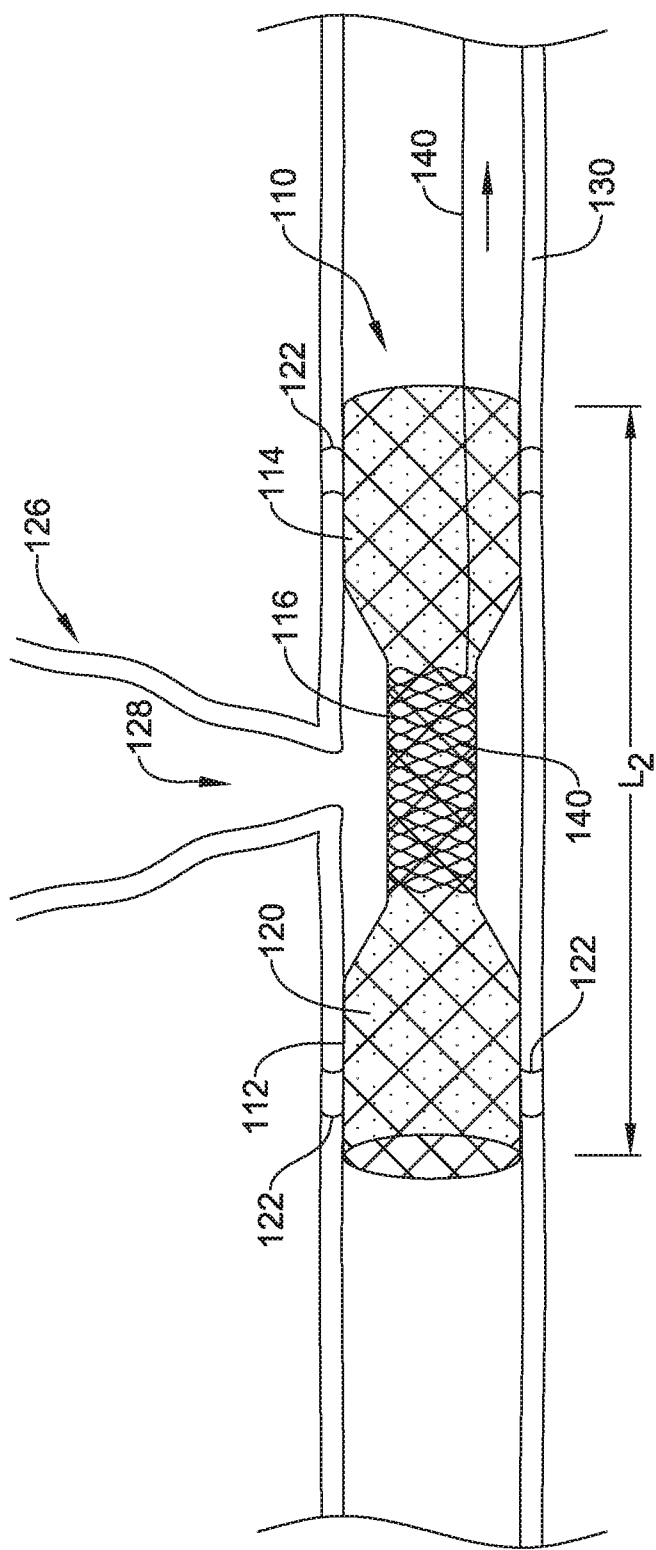
FIG. 8 illustrates the example stent of FIG. 5 being deployed adjacent the fistula.

FIG. 8 illustrates an example third step in the deployment of example stent 110. FIG. 8 illustrates an example process for removing or otherwise releasing retaining member 140, thereby releasing or constraining medial portion 116 and allowing medial portion 116 to shift from a contracted state to a radially expanded state. While not shown in FIG. 8, a first end of retaining member 140 may extend to a position outside the patient's body or otherwise be manipulated by the clinician (e.g., attached to a actuator outside the patient's body). Further, a clinician may grasp the first end of retaining member 140 and proximally retract (depicted by the arrow in FIG. 8) the retaining member 140, thereby causing it to release from medial portion 116. As retaining member 140 releases (e.g., unravels), a clinician may continue to pull it from the body lumen 130 until it is completely removed from the patient's body. In other instances, the clinician may manipulate the retaining member 140 in a different fashion to release the medial portion 116 to radially expand.

FIG. 8 further illustrates that as retaining member 140 is removed from medial portion 116, medial portion 116 may foreshorten or reduce in length as measure along the central longitudinal axis of stent 110, drawing first and second end portions 112/114 closer together. Drawing first and second end portions 112/114 closer by shortening the length of medial portion 116 may at least partially close opening 128 to fistula 126. For example, FIG. 8 shows the width of opening 128 of fistula 126 to be narrowing. In other words, as medial portion 116 shortens, the anchors 122 of stent 110 effectively pull the edges of opening 128 of fistula 126 closer together (e.g., the edges of opening 128 are drawn together). Further, the deployed length of stent member 110 is depicted as "$L_2$." At this point in the deployment process, $L_2$ is less than $L_1$ (shown in FIG. 7).

Figure 9:
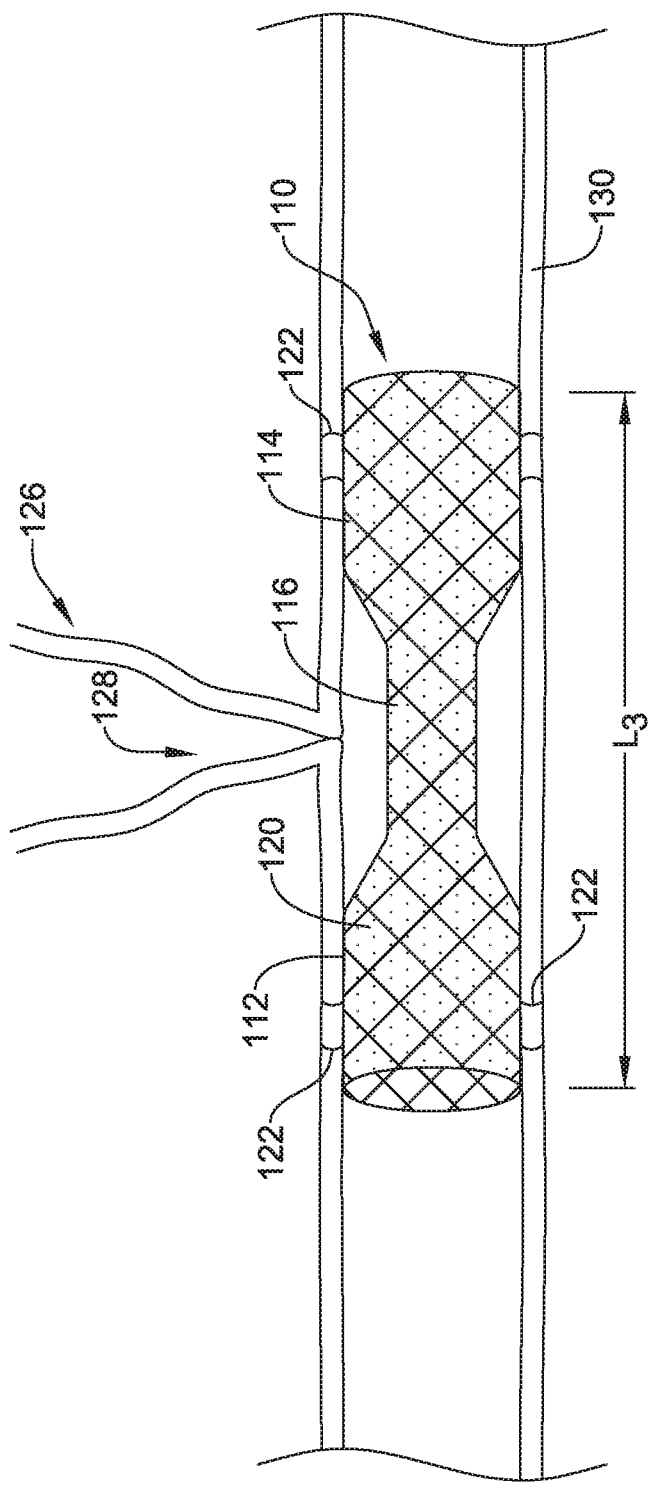
FIG. 9 illustrates the example stent of FIG. 5 deployed adjacent the fistula.

FIG. 9 illustrates stent 110 after retaining member 140 has been completely removed or released from medial portion 116. As illustrated, the width of opening 128 in fistula 126 has narrowed to a point in which opening 128 is fully closed. In other words, as medial portion 116 shortens in length, the anchors 122 of stent 110 effectively pull the edges of opening 128 of fistula 126 completely together. Further, the deployed length of stent member 110 is depicted as "$L_3$." At this point in the deployment process, $L_3$ is less than $L_2$, which is less than $L_1$. It is noted that in some instances, foreshortening of medial portion 116 may narrow opening 128, but not fully close opening 128.

It can be appreciated from FIG. 9 that when stent member 110 is fully deployed within body lumen 130 and both the first end portion 112 and second end portion 114 are sealed to the lumen wall, stent 110 may create a passageway in which digested material may pass without disturbing opening 128 of the fistula 126.

In some instances, stent 10/110 may be configured to bio-absorb or bio-degrade in the body lumen over a period of time sufficient for the fistula 126 to heal. In other instances, stent 10/110 may be removed from the body lumen after the fistula 126 has healed.

The materials that can be used for the various components of stent 10/110 (and/or other stents disclosed herein) and the various tubular members disclosed herein may include those commonly associated with medical devices. For simplicity purposes, the following discussion makes reference to stent 10/110 and other components of stent 10/110. However, this is not intended to limit the devices and methods described herein, as the discussion may be applied to other similar tubular members and/or components of tubular members or devices disclosed herein.

Stent 10/110 and/or other components of stent 10/110 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, blends, combinations, copolymers thereof, polymer/metal composites, and the like. Biodegradable polymers may also be used, including polyester homopolymers and copolymers such as polyglycolide, poly-L-lactide, poly-D-lactide, poly-D,L-lactide, poly(beta-hydroxybutyrate), poly-D-gluconate, poly-L-gluconate, poly-D,L-gluconate, poly(epsilon-caprolactone), poly(delta-valerolactone), poly(p-dioxanone), poly(trimethylene carbonate), poly(lactide-co-glycolide) (PLGA), poly(lactide-co-delta-valerolactone), poly(lactide-co-epsilon-caprolactone), poly(lactide-co-beta-malic acid), poly(lactide-co-trimethylene carbonate), poly(glycolide-co-trimethylene carbonate), poly(beta-hydroxybutyrate-co-beta-hydroxyvalerate),poly[1,3-bis(p-carboxyphenoxy) propane-co-sebacic acid], and poly(sebacic acid-co-fumaric acid), among others, poly(ortho ester) homopolymers and copolymers such as those synthesized by copolymerization of various diketene acetals and diols, among others, polyanhydride homopolymers and copolymers such as poly (adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy) propane anhydride] and poly[1,3-bis(p-carboxyphenoxy) hexane anhydride], among others; and amino-acid-based homopolymers and copolymers including tyrosine-based polyarylates (e.g., copolymers of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and bezyl esters of desaminotyrosyl-tyrosine), and tyrosine-, leucine- and lysine-based polyester-amides; specific examples of tyrosine-based polymers include includes polymers that are comprised of a combination of desaminotyrosyl tyrosine hexyl ester, desaminotyrosyl tyrosine, and various di-acids, for example, succinic acid and adipic acid, among others. Blends, composites, and copolymers of these polymers may be used. In some embodiments the stent 10/100 or components thereof may include or be combined with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material. Biodegradable metals, such as iron, magnesium, and alloys containing these and other degradable metals.

In at least some embodiments, portions or all of stent 10/110 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent 10/110 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of stent 10/110 to achieve the same result.

In some embodiments, a degree of Magnetic Resonance Imaging (MRI) compatibility is imparted into stent 10/110. For example, stent 10/110, or portions thereof, may be made of a material that does not substantially distort the image and create substantial artifacts (e.g., gaps in the image). Certain ferromagnetic materials, for example, may not be suitable because they may create artifacts in an MRI image. Stent 10/110, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some instances, it may be desirable to include therapeutic agents or biologically active agents on the surface or incorporated into the covering or some or all of the filaments of the stent 10/100 or components thereof. Beneficial therapeutic agents include anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, agents that interfere with endogenous vasoactive mechanisms, antibiotics, growth factors and other agents that promote healing, and biologics, among others.

Specific agents include taxanes such as paclitaxel, olimus family drugs such as sirolimus, everolimus, biolimus and tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), rifampin, minocycline, and infliximab as well as derivatives of the forgoing, among many others.

Example biologically active agents include SERCA 2 protein, monocyte chemoattractant proteins ("MCP-1") and bone morphogenic proteins ("BMPs"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMPs are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNAs encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathepsin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Example biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device for treating an intestine of a patient, comprising:
    an expandable scaffold including a first end portion, a second end portion and a medial portion extending along a longitudinal axis of the scaffold, the medial portion positioned between the first end portion and the second end portion, the expandable scaffold configured to shift from a contracted state to an expanded state;
    each of the first and second end portions including one or more anchoring members configured to anchor the first and second end portions to an inner surface of the intestine to prevent the first and second portions from shifting along the inner surface of the intestine when the first and second end portions are positioned adjacent the inner surface of the intestine in the expanded state;
    wherein the medial portion is configured to foreshorten along the longitudinal axis when shifting from the contracted state to the expanded state such that the first and second end portions are drawn closer together along the longitudinal axis as the medial portion shortens; and
    a retaining member configured to retain the medial portion in a contracted state while the first and second end portions expand to the expanded state, wherein the retaining member includes a filament having a first end extending to a position longitudinally beyond the expandable scaffold.

2. The medical device of claim 1, wherein the medial portion is configured to be spaced away from the inner surface of the intestine when the first and second end portions are expanded.

3. The medical device of claim 1, wherein releasing the retaining member foreshortens the medial member along the longitudinal axis to draw the first and second end portions closer together in the expanded state.

4. The medical device of claim 3, wherein the filament substantially surrounds the medial portion such that the medial portion is prevented from foreshortening before the first and second end portions have at least partially shifted to the expanded state.

5. The medical device of claim 1, wherein the filament has a length such that the first end of the filament extends to a position outside of the patient when the expandable scaffold is positioned within the intestine.

6. A medical stent for treating a body lumen, comprising:
    an expandable scaffold including a first end portion, a second end portion and a medial portion extending along a longitudinal axis of the scaffold, the medial portion positioned between the first end portion and the second end portion, the expandable scaffold configured to shift from a contracted state to an expanded state;
    each of the first and second end portions having an outer diameter when fully expanded in the expanded state greater than an outer diameter of the medial portion when fully expanded in the expanded state;
    wherein the medial portion is configured to foreshorten along the longitudinal axis when shifting from the contracted state to the expanded state such that the first and second end portions are drawn closer together along the longitudinal axis as the medial portion shortens; and
    a retaining member configured to retain the medial portion in the contracted state while the first and second end portions expand to the expanded state;
    wherein the retaining member is removable from the medial portion in situ.

7. The medical stent of claim 6, wherein releasing the retaining member foreshortens the medial portion along the longitudinal axis to draw the first and second end portions closer together in the expanded state.

8. The medical stent of claim 7, wherein the retaining member includes a filament that substantially surrounds the medial portion such that the medial portion is prevented from foreshortening before the first and second end portions have at least partially shifted to the expanded state.

9. The medical stent of claim 6, further comprising a filament knitted around the medial portion of the expandable scaffold.

10. The medical stent of claim 9, wherein the filament is configured to be unraveled to permit the medial portion to expand to the expanded state.

11. A medical stent for treating a body lumen, comprising:
    an expandable scaffold including a first end portion, a second end portion, and a medial portion extending along a longitudinal axis of the scaffold, the medial portion positioned between the first end portion and the second end portion, the expandable scaffold being configured to shift from a contracted state to an expanded state;
    each of the first and second end portions having an outer diameter when fully expanded in the expanded state greater than an outer diameter of the medial portion when fully expanded in the expanded state;

wherein the medial portion is configured to foreshorten along the longitudinal axis when shifting from the contracted state to the expanded state such that the first and second end portions are drawn closer together along the longitudinal axis as the medial portion shortens;

means for holding the medial portion in the contracted state in situ until after the first and second end portions are fully expanded, said means being configured to release the medial portion after the first and second end portions are fully expanded in situ.

12. The medical stent of claim 11, wherein said means extends outside of the body lumen when the first and second end portions are fully expanded within the body lumen.

13. The medical stent of claim 11, wherein said means substantially surrounds the medial portion such that the medial portion is prevented from foreshortening before the first and second end portions have shifted to the expanded state.

14. The medical stent of claim 11, wherein releasing the medial portion permits the medial portion to foreshorten along the longitudinal axis to draw the first and second end portions closer together in the expanded state.

15. The medical stent of claim 11, wherein each of the first and second end portions include one or more anchoring members extending radially outward from an outer surface of the first and second end portions, the one or more anchoring members being configured to anchor the first and second end portions to an inner surface of the body lumen to prevent the first and second portions from shifting along the inner surface of the body lumen when the first and second end portions are positioned against the inner surface of the intestine in the expanded state.

* * * * *